(12) United States Patent
Heineke et al.

(10) Patent No.: US 6,716,789 B1
(45) Date of Patent: Apr. 6, 2004

(54) METHOD FOR PRODUCING OXIDIC CATALYSTS CONTAINING COPPER WITH OXIDATION NUMBER>0

(75) Inventors: Daniel Heineke, Maikammer (DE); Ruprecht Meissner, Weisenheim (DE); Michael Hesse, Worms (DE); Henning-Peter Gehrken, Münster (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,988

(22) PCT Filed: Dec. 21, 1998

(86) PCT No.: PCT/EP98/08388

§ 371 (c)(1), (2), (4) Date: Jun. 21, 2000

(87) PCT Pub. No.: WO99/32224

PCT Pub. Date: Jul. 1, 1999

(30) Foreign Application Priority Data

Dec. 22, 1997 (DE) .......................................... 197 57 297

(51) Int. Cl.$^7$ ........................... B01J 21/08; B01J 23/72; B01J 23/76; C07C 49/603
(52) U.S. Cl. ....................... 502/243; 502/159; 502/240; 502/244; 502/344; 502/345; 568/360; 568/361; 568/376
(58) Field of Search ................................ 502/159, 240, 502/243, 244, 344, 345; 568/360, 361, 376

(56) References Cited

U.S. PATENT DOCUMENTS 5,472,926 A 12/1995 Gubitosa et al. ............ 502/337
5,516,851 A 5/1996 Flick et al. .................. 525/330

FOREIGN PATENT DOCUMENTS

| GB | 1081491 | 8/1967 |
| SU | 465 217 | 8/1975 |
| SU | 522 853 | 9/1976 |
| WO | WO 98/10864 | 3/1998 |

OTHER PUBLICATIONS

K. Weissermel et al. "Industrielle Organische Chemie" Verlag Chemie (1994) pp. 273–278 (1) (2).

Chang et al. "Dependance of selectivity on the preparation method of copper/∝–alumina catalysts in the dehydrogenation of cyclohexanol" Applied Catalysts A. vol. 103, (1993) pp. 233–242 (2).

Jeon et al. "Preparation and characterization of silica–supported copper catalysts for the dehydrogenation of cyclohexanol to cyclohexanone" Applied Catalysts vol. 115 (1994) pp. 29–44 (2).

Jeon et al. "Active and Selective Copper Catalysts Supported on Alkali–doped Silica for the Dehydrogenation of Cyclohexanol to Cyclohexanone" Korean Journal of Chem. Eng. vol. 12, (1995) pp. 132–133 (2).

*Primary Examiner*—Elizabeth D. Wood
(74) *Attorney, Agent, or Firm*—Keil & Weinkauf

(57) ABSTRACT

The disclosure is directed to a process for preparing an oxidic catalyst comprising copper in an oxidation state >0, which comprises treating a solid oxidic support material with an aqueous solution comprising at least one copper salt and at least one organic water soluble polymer which binds copper ions coordinatively in a concentration of from 0.1 to 100 g/l and then calcining, to the catalyst obtainable by this process and also to a process for dehydrogenating secondary alcohols to ketones using the catalysts, especially for dehydrogenating cyclohexanol.

8 Claims, No Drawings

METHOD FOR PRODUCING OXIDIC CATALYSTS CONTAINING COPPER WITH OXIDATION NUMBER>0

The present invention relates to a process for preparing oxidic catalysts comprising copper in an oxidation state >0 by treatment of a solid oxidic support material with an aqueous copper salt solution and subsequent calcination. The present invention also relates to the catalysts obtainable by this process and to their use for dehydrogenating secondary alcohols to the ketones, especially for dehydrogenating cyclohexanol to cyclohexanone.

The catalytic dehydrogenation of secondary alcohols is widely used in industry for producing ketones, for example for the production of cyclohexanone from cyclohexanol (see for example K. Weissermel, H.-J. Arpe, Industrielle Organische Chemie, 4th edition Verlag Chemie, Weinheim, 1994, p. 274). These processes are known in numerous variations (excepting the embodiment of the present invention) and therefore need only be explained in principle. The processes typically involve passing the alkanol, or an alkanol/ketone mixture, over a copper catalyst at elevated temperature, generally above 200° C. Here it is important to note that the catalytic dehydrogenation of alcohols to ketones is reversible and that the position of the equilibrium will shift toward the starting materials with decreasing temperature. Furthermore, equilibration is slow at a low temperature, making it generally impossible to achieve all but low conversions. If, in contrast, the process is carried out at elevated temperature, for example at above 400° C., lower selectivities to the product of value are obtained, since side reactions, for example dehydration of the alcohols or dimerization of the product ketones, will take place at these temperatures to an appreciable extent in some instances.

Alkanols are frequently dehydrogenated at below 400° C. using catalysts comprising copper as an active component on a solid, usually oxidic support. The copper content of such catalysts can be up to 50% by weight, based on the total weight of the catalyst. Typical support materials of oxidic type are ceramic oxides such as silicon dioxide, e.g., silica, silicates, alumosilicates, aluminum oxide, zirconium dioxide and titanium dioxide, also zeolites and pumice. As well as copper as active component, prior art catalysts frequently comprise a small amount of alkali metals as promoters.

GB-A-1081491 discloses $Cu/Al_2O_3$, SU-A 465 217 discloses $Cu/Li/SiO_2$ and SU-A 522853 discloses $Cu/K/Al_2O_3$ for the nonoxidative dehydrogenation of cyclohexanol. The copper catalysts in question are usually prepared by applying the active copper component either to a prefabricated support, by precipitation of a copper salt or by impregnation with a suitable copper salt solution, or by coprecipitating the components making up the catalyst.

Chang et al. (Appl. Catal. A 103 (1994), 233–42) describe copper catalysts for the dehydrogenation of cyclohexanol to cyclohexanone which are obtainable by reductive precipitation of copper on $\alpha$-$Al_2O_3$ as support. Reductive precipitation has the disadvantage that, in general, the support first has to be seeded with a noble metal such as platinum, rhodium, iridium, gold or palladium in order that uniform deposition of copper on the support may be achieved. This creates additional costs. In addition, the catalysts described by Chang et al. are difficult-to-tablet powders having limited processibility into shaped articles such as tablets. These catalysts are therefore not suitable for industrial use.

Chung et al. (Appl. Catal. A 115 (1994), 29–44) further describe copper catalysts which are obtainable by alkali precipitation of copper from an aqueous copper salt solution onto a silicon dioxide support. True, the catalysts obtainable by the process described therein have comparatively high selectivity, but their activity is too low for the desired applications.

In addition, prior art catalysts lose activity with increasing time on stream. Consequently, in a prolonged run, the operating temperature of the reactor has to be continually raised, entailing a loss of selectivity. Moreover, raising the temperature speeds up the deactivation of the catalyst.

It is an object of the present invention to provide a catalyst for the nonoxidative dehydrogenation of secondary alcohols to the corresponding ketones which combines high activity with high selectivity. In addition, the catalyst shall not lose its activity in prolonged operation. Moreover, the catalyst shall be economical to obtain and have advantageous mechanical properties.

We have found that this object is achieved by catalysts which are obtainable by treating a solid oxidic support material with aqueous copper salt solutions comprising at least one organic water soluble polymer which binds copper ions coordinatively and subsequent calcination.

The present invention accordingly provides a process for preparing an oxidic catalyst comprising copper in an oxidation state>0, which comprises treating a solid oxidic support material with an aqueous solution comprising at least one copper salt and at least one organic water soluble polymer which binds copper ions coordinatively in a concentration of from 0.1 to 100 g/l and then calcining. The present invention further provides the catalysts obtainable by this process.

According to the invention, suitable water soluble polymers which bind copper ions coordinatively either have carboxylate groups or have amino groups and/or carboxamide groups. Polymers containing carboxylate groups are customarily homo- or copolymers of ethylenically unsaturated carboxylic acids, for example homo- and copolymers of acrylic acid, methacrylic acid, crotonic acid, maleic acid, fumaric acid and itaconic acid. In general, suitable polymers containing carboxylate groups contain not less than 50 mol %, based on the total number of constitutive monomers, of the aforementioned ethylenically unsaturated carboxylic acids.

Suitable comonomers are in particular monomers having a high solubility in water (i.e., >60 g/l at 25° C.), for example the amides of the aforementioned ethylenically unsaturated carboxylic acids, N-vinyllactams and the hydroxyalkyl esters of the aforementioned ethylenically unsaturated carboxylic acids. Preferred polymers containing carboxylate groups are acrylic acid homopolymers and copolymers.

Typical polymers containing amide groups are the homo- and copolymers of amides of monoethylenically unsaturated carboxylic acids, for example polymers of acrylamide and/or of methacrylamide. In general, such polymers containing at least 50 mol % of units derived from monomers contain amide groups in polymerized form. Suitable comonomers are the aforementioned ethylenically unsaturated carboxylic acids or N-vinyllactams. A further class of polymers containing amide groups contain not less than 50 mol % of units derived from N-vinyllactams such as N-vinylpyrrolidone, N-vinylcaprolactam and N-vinylpiperidone. Suitable comonomers for N-vinyllactams are the aforementioned ethylenically unsaturated carboxylic acids, their amides, their hydroxyalkyl esters, vinyl acetate, vinyl propionate and vinyl-substituted nitrogenous heterocycles such as vinylpyridines and vinylimidazole.

Amino-containing polymers include not only homo- and copolymers of amino-containing monomers but also such polymers as are obtainable by polymer-analogous conversion of functional groups into amino functions. Examples of the first monomers are homo- and copolymers of aminoalkyl acrylates and methacrylates such as N,N-dimethylaminoethyl acrylate and N,N-dimethylaminoethyl methacrylate, of vinylpyridines and of vinylimidazoles. Suitable comonomers for the amino-containing monomers are, for example, the amides of ethylenically unsaturated carboxylic acids, N-vinyllactams and vinyl-substituted nitrogenous heterocycles. Polymers whose amino groups are obtainable by polymer-analogous reaction of functional groups on the polymer include the hydrolysis products of polymers based on N-vinylamides, for example the hydrolysis products of homo- and copolymers of N-vinylacetamide, and also the hydrogenation products of polymers based on ethylenically unsaturated nitrites, for example the hydrogenation products of homo- and copolymers of acrylonitrile and of methacrylonitrile.

The water soluble polymers used according to the present invention generally have a weight average molecular weight $M_w$>500 dalton and up to $10^6$ dalton. Water soluble polymers which are preferred according to the present invention have a molecular weight $M_w$ within the range from 1000 to 100,000, especially within the range from 2000 to 50,000, particularly preferably within the range from 5000 to 30,000 dalton. They are well known to the person skilled in the art and commercially available or preparable by known processes.

Preference according to the present invention is given to homo- and copolymers of N-vinyllactams, especially of N-vinylpyrrolidone. Of these, preference is given to the homo- and copolymers, especially the homopolymers, having a weight average molecular weight within the range from 1000 to 100,000, especially within the range from 2000 to 50,000 and most preferably within the range from 5000 to 30,000. Homo- and copolymers of N-vinyllactams are well known to the person skilled in the art, for example from Ullmann's Encyclopedia of Industrial Chemistry, 5th ed, Vol A21, p. 752–756, and also from Römpp, Chemielexikon, 9th edition, Georg-Thieme-Verlag, Stuttgart, 1989–1992, p. 3583 f. and also references cited therein (see also Davidson, Handbook of Water-Soluble Gums and Resins, McGraw-Hill, New York-London 1980, p. 21.1–21.21; Houben-Weyl, E20/2, 1267–1276).

In the process of the present invention, the copper is applied to the solid oxidic support by treating the support with an aqueous solution comprising at least one copper salt and at least one water soluble polymer in the above-specified amount. The copper is applied in such a way that it separates out on the solid oxidic support in an oxidation state >0.

The inventive treatment of the solid oxidic support of the aqueous copper salt solution can in principle be effected in two different ways. In one embodiment of the present invention, the solid oxidic support is impregnated with the aqueous copper salt solution comprising the water soluble polymer, dried and, if necessary, subjected to this operation again until the desired copper content is obtained. The impregnating can be effected, for example, by spraying the solid oxidic support with the aqueous copper salt solution in a fluidized bed. Examples of suitable apparatus include coating pans and fluidized bed granulators. It is further possible to impregnate the solid oxidic support by suspending it in an aqueous solution of the copper salt and of the water soluble polymer, filtering and drying (see below), if necessary repeatedly until the desired copper content is achieved.

In a preferred embodiment of the process of the present invention, the copper is applied by using a precipitant to precipitate the copper onto the solid oxidic support. In general, the solid oxidic support is suspended in an aqueous solution comprising at least one copper salt and at least one water soluble polymer and then a precipitant is added. Both the copper salt and the water soluble polymer can also be added in dissolved form or as solids to an aqueous suspension of the solid oxidic support. What is essential for the present invention is that the polymer and the copper salt are present in dissolved form in the aqueous dispersion of the support before the precipitant is added. After precipitation, the resulting solid (support material with precipitated copper compound) is filtered off and dried. Before the resulting solid is dried, it may be washed with water or a water miscible organic solvent to remove excess precipitant. It is generally dried at above 100° C. and at atmospheric pressure. However, it can also be dried under reduced pressure and, if desired, a low temperature. The drying time generally ranges from 1 to 48 h. The drying temperature will generally not exceed 200° C.

Suitable precipitants include aqueous solutions of water soluble salts comprising phosphate, sulfide, carbonate, oxalate or hydroxide ions in a concentration sufficient to precipitate the copper. Addition of the precipitant precipitates the copper as a sparingly soluble salt on the solid oxidic support. In contrast to electroless coppering, here the copper is present in an oxidation state>0. Typical precipitants include the alkali metal salts of the aforementioned anions, especially the sodium and potassium salts. Sulfide ions can also be used in the form of hydrogen sulfide.

Preferred precipitants for aqueous solutions of water soluble carbonates and of hydroxides, for example aqueous solutions of sodium carbonate, potassium carbonate, sodium hydroxide and potassium hydroxide. The most preferred precipitants are aqueous solutions of sodium carbonate or of potassium carbonate.

The precipitation can be carried out both at room temperature and at elevated temperature. The precipitation is preferably carried out at above 50° C., especially if carbonate or hydroxide is used as precipitant. The precipitant is preferably added not all at once, but over a prolonged period, preferably within 0.5 to 10 h, especially within 1 to 5 h.

The process of the present invention is generally operated using oxidic support materials selected from ceramic oxides such as silicon dioxide, for example silicas and silica gels, silicates, alumosilicates, aluminum oxide, especially α-alumina, zirconium dioxide and titanium dioxide or mixtures thereof, and also zeolites and pumice. Support materials preferred for the present invention comprise not less than 80% by weight of silicon dioxide, for example in the form of a silica gel or in the form of a silica. The oxidic support materials used for the present invention generally have a specific BET surface area (as measured according to German Standard Specification DIN 66131) of above 30 $m^2/g$, preferably above 50 $m^2/g$, especially above 100 $m^2/g$. In general, the BET surface area will not exceed 600 $m^2/g$, especially 500 $m^2/g$. In an advantageous embodiment of the present invention, the oxidic support material used is a silica having a BET surface area within the range from 200 to 400 $m^2/g$.

The aqueous copper salt solutions used for the process of the present invention generally comprise a water soluble copper salt in a concentration of from 0.05 to 5 mol/l, preferably from 0.1 to 3 mol/l (based on the aqueous phase prior to addition of the precipitant or on the copper solution used as impregnant). The concentration generally depends on the solubility of the copper salt or is decided on grounds of practicability. Typical copper salts are copper(II) acetate, copper(II) chloride, copper(II) sulfate, copper(II) nitrate and also the corresponding hydrates of these salts. The concentration of the water soluble polymer in these solutions is generally within the range from 0.1 to 100 g/l, preferably within the range from 0.5 to 50 g/l, particularly preferably within the range from 1 to 10 g/l. The ratio of copper to polymer is generally within the range from 100:1 to 1:2, preferably within the range from 50:1 to 1:1, especially within the range from 20:1 to 2:1 (weight ratio of copper:polymer).

The inventive treatment of the solid oxidic support material with the aqueous copper salt solution may be followed by a calcining step. The calcining step is preferably carried out in air or in an inert gas atmosphere, advantageously in nitrogen, at from 250 to 450° C. The calcining step generally takes from 1 to 24 h.

The catalyst powder obtained from the process of the present invention is preferably compacted into shaped articles such as tablets, strands, rings, wagon wheels, stars, monoliths, balls, granules or extrudates, preferably tablets, generally by admixture of tableting aids. The customary tableting aids can be used. Examples are graphite, magnesium stearate, methylcelluloses (such as Walocel®), copper powder or mixtures thereof. The shaped articles can be formed before or after the calcining step.

The copper content of a catalyst (reckoned as metallic copper) will usually be within the range from 0.01 to 50% by weight, preferably within the range from 2 to 30% by weight, particularly preferably within the range from 5 to 20% by weight, based on the total weight of the catalyst material. The catalysts of the present invention may further comprise up to 2% by weight of alkali metals, especially sodium or potassium, from the process of making them. The BET surface area (as measured according to German Standard Specification DIN 66131) of the catalyst is generally not below 30 $m^2/g$, preferably within the range from 50 to 600 $m^2/g$, particularly preferably within the range from 100 to 500 $m^2/g$. In an advantageous embodiment, it is within the range from 200 to 400 $m^2/g$. The average particle size of the copper salt deposited according to the present invention on the catalyst support is generally below 20 nm. The particle size can be determined, for example, by transmission electron microscopy or by determination of the size of the crystalline regions by x-ray diffraction (XRD) analysis.

The catalysts of the present invention can be used for dehydrogenating secondary alcohols to the corresponding ketones. The secondary alcohols can be not only open chain alcohols but also cycloalkanols. Preferred starting materials for the process of the present invention are alkanols and cycloalkanols having from 3 to 14 carbon atoms. Particularly preferred starting materials are cycloalkanols such as cyclopentanol, cyclohexanol, methylcyclohexanols and cyclododecanol. The catalysts of the present invention are very particularly suitable for dehydrogenating cyclohexanol.

The starting materials for the dehydrogenation can take the form not only of pure alcohols but also the form of mixtures of different alcohols. Frequently, mixtures of alcohol and the dehydrogenation product are used as well. The starting material for the dehydrogenation of cyclohexanol is generally a mixture of cyclohexanol and cyclohexanone. Pure cyclohexanol can also be used. The mixture to be used usually comprises from 50 to 100%, preferably from 60 to 99%, especially 96%, by weight of cyclohexanol and from 50 to 0%, preferably from 40 to 1%, especially 4%, by weight of cyclohexanone. Cyclohexanone and cyclohexanol are usually obtained by oxidation of cyclohexane and subsequent concentrating of the cyclohexanol by distillative removal of cyclohexanone and of other low boilers.

The dehydrogenation of the secondary alcohols to the ketones is generally carried out in the gas phase at from 180 to 400° C., preferably within the range from 200 to 350° C., particularly preferably within the range from 220 to 260° C. The pressure is generally selected within the range from 50 kPa to 5 MPa, and atmospheric pressure is employed in particular.

In general, the catalyst is activated with hydrogen before the actual reaction (formation phase). This is generally done by passing a hydrogen stream diluted with an inert gas, preferably nitrogen, over the catalyst at a certain temperature, preferably within the range from 120 to 300° C. The hydrogen content of the reducing gas is then customarily increased continuously until there is no further significant change in the temperature.

In a preferred embodiment, the starting material is passed as a gas over the catalyst at a liquid hourly space velocity (LHSV) of preferably from 0.1 to 100 $h^{-1}$, particularly preferably of from 0.1 to 20 $h^{-1}$. The starting material can be mixed with an inert gas such as nitrogen or with steam. The dehydrogenation product can be worked up in a conventional manner (for cyclohexanone see, for example, DE-A 1,296,625 and DE-A 1,443,462) for further processing.

In a further preferred embodiment, hydrogen is separated from the reaction mixture leaving the reaction zone and added to the gas mixture entering the reaction zone. It is further advantageous to recycle the reaction mixture until the desired conversion is achieved.

The catalyst of the present invention is very active and can therefore be operated at significantly lower temperatures than catalysts currently used in industry, is quick to activate and gives high selectivity and conversions close to the equilibrium. In addition, noticeable deactivation occurs only after distinctly longer periods than hitherto customary with existing catalysts.

The catalyst of the present invention is notable for good tabletability, adequate hardness, high conversions at low operating temperatures, high cyclohexanone selectivities and a long on stream life.

EXAMPLES

I. Preparation of Catalysts According to Invention
(Inventive Example 1)

271 g of silicon dioxide having a BET surface area of 270 $m^2/g$ were suspended in one liter of deionized water. 5 g of polyvinylpyrrolidone (PVP from Merck, order #7443, average molecular weight 25,000 g/mol) and 339 ml of 2M aqueous copper nitrate solution were added. The suspension was heated to 90° C. 3000 ml of a concentrated aqueous sodium carbonate solution were then added at 90° C. over 4 hours until a constant pH of about 9.6 was reached. The batch was cooled down to room temperature, and the resulting grayish black suspension was filtered off and washed with 80 l of water. The powder was then dried at 120° C. for 16 hours. Thereafter it was calcined at 300° C. for 2 hours.

Elemental analysis of the catalyst powder thus prepared (atomic absorption spectroscopy) revealed a copper content of 15.1% by weight (reckoned as elemental copper) and 1.0% by weight of sodium (likewise reckoned as elemental sodium).

Examination of the catalyst powder by means of transmission electron microscopy showed that the deposited copper particles were essentially below 10 nm in diameter.

100 g of the catalyst powder obtained in Example 1 were precompacted with 3 g of graphite and 1 g of magnesium stearate into tablets 20 mm in diameter and 2 mm in thickness. The tablets were then forced through a screen having a mesh size of 1 mm and were press molded into tablets 5 mm in diameter and 3 mm in thickness. The side crushing strength of the tablets was 36±4 N. The side crushing strength was determined using an instrument from Frank, model #81557.

Comparative Example 1

133.93 g of copper(II) nitrate trihydrate were suspended in 1500 ml of distilled water together with 200 g of silicon dioxide (BET surface area 372 $m^2/g$). The suspension was heated to 80° C. 500 ml of 0.3 N aqueous potassium hydroxide solution were added dropwise over 2 hours at 80° C. 4200 ml of 0.3 N aqueous potassium hydroxide solution were then added over 4 hours until a constant pH of about 9.5 was reached. The temperature of 90° C. was maintained for four hours while stirring. The grayish black catalyst was then filtered off and dried at 120° C. for 8 hours. It was then calcined at 300° C. for 5 hours.

Elemental analysis of the catalyst powder thus prepared (atomic absorption spectroscopy) revealed a copper content of 14.3% by weight (reckoned as elemental copper) and 3.3% by weight of potassium (likewise reckoned as elemental potassium).

Examination of the catalyst powder by means of transmission electron microscopy showed that the deposited copper particles were essentially below 150 nm in diameter.

The catalyst powder thus obtained was press molded together with 1.5 g of graphite in the above-described manner to form tablets 5×4 mm in size. The side crushing strength of the tablets was 60±8 N.

II. Catalyst Test

The catalyst tests were carried out in a tubular reactor 5 cm in diameter and 60 cm in length. For each test, 200 ml of the catalyst of I were installed and activated with hydrogen before the reaction. The catalyst was activated with 150 l of $N_2$/h and 1.5 l of $H_2$/h at 120° C. before the starting material was introduced. The hydrogen stream was stopped as soon as the temperature rose by more than 10° C. The temperature was then raised in 20° C. increments to 200° C. while the hydrogen rate was kept constant. At 200° C. the catalyst was then activated with 150 l of $N_2$/h and 7.5 l of $H_2$/h. After activation, the catalyst was subjected to a 96% cyclohexanol/4% cyclohexanone mixture at an LHSV of about 0.7 $h^{-1}$. The reactor exits streams were analyzed by gas chromatography after various times. The results are summarized in Table 1.

TABLE 1

| Catalyst | Temperature [° C.] | Time [h] | Conversion [%] | Selectivity [%] |
|---|---|---|---|---|
| Inventive Example 1 | 217 | 34 | 49 | 99.4 |
| | 221 | 106 | 47 | 99.6 |

TABLE 1-continued

| Catalyst | Temperature [° C.] | Time [h] | Conversion [%] | Selectivity [%] |
|---|---|---|---|---|
| | 234 | 322 | 48 | 99.4 |
| | 235 | 466 | 50 | 99.9 |
| | 235 | 562 | 51 | 99.9 |
| Comparative Example 1 | 224 | 34 | 7 | 99.4 |
| | 236 | 58 | 12 | 99.5 |
| | 237 | 106 | 10 | 99.4 |
| | 237 | 226 | 10 | 99.5 |
| | 236 | 346 | 9 | 99.3 |

The catalyst of the present invention gives a conversion close to the equilibrium at a very high selectivity of >99% at as low as >220° C. At this temperature, the catalyst is observed to deactivate only very gradually, as is evidenced by the small increase in temperature required to maintain the conversion.

We claim:

1. A process for preparing an oxidic catalyst comprising copper in an oxidation state >0, which comprises treating a solid oxidic support material with an aqueous solution comprising at least one copper salt and at least one organic water soluble polymer which binds copper ions coordinatively in a concentration of from 0.1 to 100 g/l and then calcining, wherein the copper is applied to the solid oxidic support material by precipitation from the aqueous solution using a precipitant and wherein the water soluble polymer is an N-vinylpyrrolidone homopolymer or copolymer.

2. A process as claimed in claim 1, wherein the precipitation is carried out at a temperature above 50° C.

3. A process as claimed in claim 1, wherein the oxidic support material has a BET surface area >50 $M^2/g$ (as measured according to DIN 66131).

4. A process as claimed in claim 1, wherein the oxidic support material comprises at least 70% by weight of $SiO_2$, based on the total weight of the support material.

5. A process as claimed in claim 1, wherein the copper is applied to the support material in an amount of from 0.1 to 50% by weight, based on the total weight of the catalyst.

6. A catalyst comprising copper in an oxidation state >0, obtained by a process as claimed in claim 1, wherein the average particle size of the copper deposited on the solid oxidic support material support is below 20 nm and wherein the catalyst further comprises up to 2% by weight of alkali metals.

7. A process for dehydrogenating a secondary alcohol to the corresponding ketone, which comprises dehydrogenating the secondary alcohol over the catalyst as claimed in claim 6.

8. A process as claimed in claim 7, wherein the secondary alcohol is cyclohexanol.

* * * * *